(12) United States Patent
Beckmann et al.

(10) Patent No.: US 8,476,904 B2
(45) Date of Patent: Jul. 2, 2013

(54) METHOD FOR MAGNETIC RESONANCE IMAGING

(75) Inventors: Marc Beckmann, Erlangen (DE); Cheng Ni, Shenzhen (CN); Xiao Dong Zhou, Shenzhen (CN)

(73) Assignee: Siemens Aktiengesellschaft, Munich (DE)

( * ) Notice: Subject to any disclaimer, the term of this patent is extended or adjusted under 35 U.S.C. 154(b) by 288 days.

(21) Appl. No.: 13/052,626

(22) Filed: Mar. 21, 2011

(65) Prior Publication Data

US 2011/0241668 A1 Oct. 6, 2011

(30) Foreign Application Priority Data

Mar. 30, 2010 (CN) .......................... 2010 1 0135507

(51) Int. Cl.
*G01V 3/00* (2006.01)
(52) U.S. Cl.
USPC .......................................... 324/309; 324/307

(58) Field of Classification Search
USPC ........................... 324/300–322; 600/407–445
See application file for complete search history.

(56) References Cited

U.S. PATENT DOCUMENTS

| | | | | |
|---|---|---|---|---|
| 6,836,114 B2 * | 12/2004 | Reddy et al. | .................. | 324/307 |
| 7,521,930 B2 | 4/2009 | Li et al. | | |
| 2011/0092801 A1 * | 4/2011 | Gross et al. | .................. | 600/412 |
| 2012/0049846 A1 * | 3/2012 | Gross et al. | .................. | 324/309 |

* cited by examiner

*Primary Examiner* — Brij Shrivastav
(74) *Attorney, Agent, or Firm* — Schiff Hardin LLP

(57) ABSTRACT

A method for magnetic resonance imaging, in which a magnetic resonance imaging device employs a multi-echo imaging sequence, includes the steps of: applying, to one of the multiple echoes, a first number of steps of phase encoding, applying a readout gradient, and collecting the data of this echo to reconstruct an anatomical image; and applying, to another one of the multiple echoes, a second number of steps of phase encoding, applying a readout gradient, and collecting the data of this echo to construct a temperature image. The method is capable of obtaining at the same time both a temperature image with high time resolution and an anatomical image with high spatial resolution.

12 Claims, 2 Drawing Sheets

METHOD FOR MAGNETIC RESONANCE IMAGING

BACKGROUND OF THE INVENTION

1. Field of the Invention

The present invention relates to the technical field of magnetic resonance imaging, and in particular, to a method for magnetic resonance imaging.

2. Description of the Prior Art

During a heating operation to a target area monitored by magnetic resonance imaging (MRI), a magnetic resonance imaging device can monitor the temperature changes of the target area so as to monitor the process and effects of the heating in real time. A common method for temperature measurement in magnetic resonance imaging is to perform a temperature imaging utilizing the fact that the proton resonance frequency (PRF) in water skews as the temperature changes so as to obtain a temperature image. Generally, a gradient echo sequence is utilized to perform a PRF skew-based magnetic resonance temperature imaging. In order to monitor the temperature of the target area in real time, it is required that the time resolution of the temperature imaging sequence be very high. In order to achieve this object, in the prior art the parameters of the temperature imaging sequence are optimized and short repeat time (TR), low spatial resolution, etc. are utilized. However, at the same time, from the viewpoint of the applications, it is also necessary to have an anatomical image with relatively high spatial resolution for monitoring the position of the heated target area and the anatomical image of the target area must be capable of being updated in a timely manner during the heating process.

Generally, when using magnetic resonance temperature imaging to monitor heating, the data generated by the temperature imaging sequence is used to reconstruct an anatomical image, thus monitoring the target area. Since the parameter settings of the temperature imaging sequence have had the imaging time optimized, for example, by applying relatively few steps of phase encoding, the object of quick temperature monitoring is achieved. Since there are only a few steps of phase encoding, an anatomical image rebuilt on the basis of the data generated by the temperature imaging sequence has relatively low resolution and the contrast between tissues is relatively poor, therefore the requirements relating to the differentiation and location of the tissues and organs in the target area during the heating process cannot be fully satisfied. It can be seen that the currently available temperature imaging sequence for magnetic resonance imaging cannot satisfy at the same time the requirements relating to a high spatial resolution and a high time resolution.

In Chinese patent application 200710064914.4, by the inventors Li Guo-bin, Chung Yiu-Cho, Zhang Qiang, and Zhou Xiao-dong (corresponding to U.S. Pat. No. 7,521,930), in order to balance the time resolution and the spatial resolution of a temperature image, there is provided a method for accelerating the magnetic resonance temperature imaging. In that patent application, the method first determines a temperature change at an ultrasonic focus, then determines the ideal acceleration rate needed by the data collection, adjusts the variable density data sampling of K space, and reconstructs the data obtained by the sampling to form a temperature image.

SUMMARY OF THE INVENTION

An object of the present invention is to provide a method for magnetic resonance imaging, which obtains at the same time a temperature image with high time resolution and an anatomical image with high spatial resolution.

Accordingly, the present invention provides a method for magnetic resonance imaging, in which a magnetic resonance imaging device employs a multi-echo imaging sequence, and the method includes:

applying to one echo of the multiple echoes a first number of steps of phase encoding, applying a readout gradient, and collecting the data of this one echo to reconstruct an anatomical image, and applying to another echo of the multiple echoes a second number of steps of phase encoding, applying a readout gradient, and collecting the data of this other echo to construct a temperature image.

In one embodiment, the readout gradient employs a mono-polar mode.

Preferably, the magnetic resonance imaging device merges a rephasing gradient and a dephasing gradient adjacent to the readout gradient direction as one gradient and applies the same.

In another embodiment, the readout gradient employs a bi-polar mode.

Preferably, the magnetic resonance imaging device merges two gradients adjacent to the phase encoding gradient direction as one gradient and applies the same.

Preferably, the phase encoding gradient corresponding to said one echo is different from the phase encoding gradient corresponding to the other echo.

Preferably, the readout gradient corresponding to the one echo is different from the readout gradient corresponding to the other echo.

Preferably, the one echo is the first echo of said multi-echo sequence, and the other echo is any one of said multi-echo sequence after the first echo, and preferably is the second echo of the multi-echo sequence.

In the above mentioned technical solution, the multi-echo sequence employs gradient echoes or spin echoes.

Preferably, the first number is greater than the second number. More preferably, the first number is a multiple of an integral number of the second number.

It can be seen from the above mentioned solution that, since the present invention employs a multi-echo imaging sequence, to one echo therein is applied a first, larger number of steps of phase encoding for reconstructing an anatomical image, and to another echo is applied a second, smaller number of steps of phase encoding for collecting a temperature image, so that the magnetic resonance imaging device uses different echoes to image independently, thus being able to obtain a temperature image with high time resolution and an anatomical image with high spatial resolution. Furthermore, the first number is larger than the second number, so that due to the few steps of phase encoding for the temperature image, its imaging time is saved and it has relatively high time resolution; and due to the increased number of steps of phase encoding for the anatomical image, it has relatively high spatial resolution. Accordingly, this further ensures in the present invention a temperature image with high time resolution and an anatomical image with high spatial resolution.

BRIEF DESCRIPTION OF THE DRAWINGS

FIGS. 4a to 4d are the anatomical images and the phase images (for calculating the temperature image) obtained by employing the solution of the present invention, in which FIG. 4a is a high spatial resolution image for anatomy-locating, and FIGS. 4b, 4c, and 4d are high time resolution images for calculating the temperature image, and in which the four figures to the left-hand side are magnitude images and the four figures to the right-hand side are phase images.

DESCRIPTION OF THE PREFERRED EMBODIMENTS

In order to make the objects, technical solutions and advantages of the present invention more apparent, the present invention will be further described in detail below by way of embodiments.

The present invention encompasses a method for realizing the combination of forming an anatomical image and a temperature image using a multi-echo sequence, and for each echo, a magnetic resonance imaging device performs separate imaging tasks and has independent space encodings. Preferably, the image data with low spatial resolution and high time resolution therein can be used to reconstruct the temperature image with high time resolution, and the image data with high spatial resolution and low time resolution can be used to reconstruct the anatomical image. Therefore it is realized in the present invention for an anatomical image with high spatial resolution and a temperature image with high time resolution to be obtained at the same time.

Figure 1:
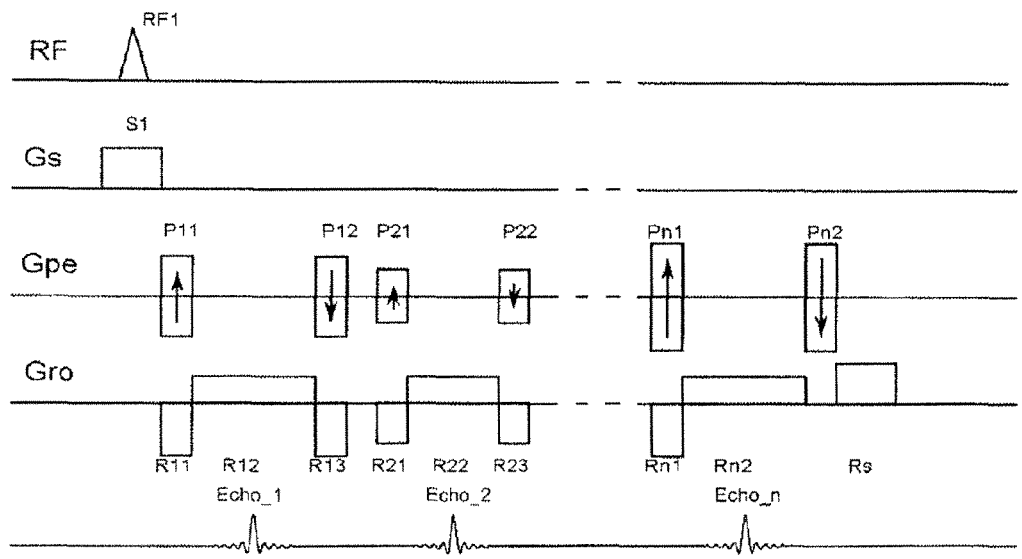
FIG. 1 is a schematic illustration of an embodiment of the present invention, in which the multi-echo sequence is formed by gradient echoes and the readout gradient employs a mono-polar mode.

As illustrated in FIG. 1, in an embodiment of the present invention, a multi-echo sequence employs gradient echoes and the readout gradient employs a mono-polar mode. In FIG. 1, RF, Gs, Gpe, and Gro respectively represent a radio frequency pulse, a slice selection gradient, phase encoding gradients and readout gradients.

In the embodiment shown in FIG. 1, the magnetic resonance imaging device first transmits a radio frequency pulse RF1, and at the same time applies a slice selection gradient S1 so as to select an imaging slice.

As to the first echo Echo_1, the magnetic resonance imaging device applies a phase encoding gradient P11 in the direction of the phase encoding gradient, and applies a dephasing gradient R11 in the direction of the readout gradient. It then applies a readout gradient R12 in the direction of the readout gradient and collects the data of the first echo Echo_1. The readout gradient R12 can be regarded as including a rephasing gradient and a dephasing gradient that are closely adjacent (not shown in detail in the figure). Finally, a phase encoding gradient P12 is applied in the direction of the phase encoding gradient, and a rephasing gradient R13 in the direction of the readout gradient.

As to the second echo Echo_2, the magnetic resonance imaging device applies a phase encoding gradient P21 in the direction of the phase encoding gradient, and a dephasing gradient R21 in the direction of the readout gradient. It then applies a readout R22 in the direction of the readout gradient and collects the data of the second echo Echo_2. In the same way the readout gradient R22 can be regarded as including a rephasing gradient and a dephasing gradient that are closely adjacent (not shown in detail in the figure). Finally, a phase encoding gradient P22 is applied in the direction of the phase encoding gradient, and a rephasing gradient R23 in the direction of the readout gradient.

The magnetic resonance imaging device subsequently performs the operations similar to the process of the first echo and the second echo, until the magnetic resonance imaging device has collected the data of the $n^{th}$ (n is an integer) echo Echo_n, and it applies a destruction gradient Rs in the direction of the readout gradient. By then, the magnetic resonance imaging device has applied a phase encoding step to each echo, applied the readout gradients, and collected the data of each echo at the first step of phase encoding.

The magnetic resonance imaging device repeats the operation shown in FIG. 1, that is, to apply a first number of phase encoding steps to the first echo, a second number of phase encoding steps to the second echo, ..., an $n^{th}$ number of phase encoding steps to the $n^{th}$ echo, and the corresponding readout gradients, and collects data of each echo so as to respectively reconstruct the images corresponding to the echoes. Taking the first echo and the second echo by way of example, if the first number is K times the second number, then during the entire imaging process, the magnetic resonance imaging device can apply the first number of steps of phase encoding to the first echo so as to obtain the image of the first echo, and apply K times the second number of steps of phase encoding to the second echo so as to obtain K images of the second echo.

In the embodiment shown in FIG. 1, in the direction of the phase encoding gradient, the magnetic resonance imaging device can merge two adjacent phase encoding gradients as one gradient and apply it to the target area, which can optimize the operation of the magnetic resonance imaging device. For example, P12 and P21, P22 and P31, ..., P(n−1)2 and Pn1 (i.e. the adjacent phase encoding gradients of adjacent echoes) are merged. In the readout gradient direction, the magnetic resonance imaging device can also merge the adjacent rephasing gradient and dephasing gradient as one gradient and apply it to the target area. For example, R13 and R21, R23 and R3I, ..., R(n−1)3 and Rn1 (i.e. the adjacent rephasing gradient and dephasing gradient of adjacent echoes) are merged.

Since each echo has an independent phase encoding gradient and frequency encoding gradient (readout gradient), the phase encoding gradients corresponding to any two echoes in the multi-echo sequence can either be the same or different, and equally the frequency encoding gradients corresponding to any two echoes can either be the same or different. It is preferable in the present invention for them to be different, therefore different frequency encoding gradients and/or frequency encoding gradients can be applied to the imaging of the anatomical image and the temperature image. For example, as shown in FIG. 1, P11 and P12 are different from P21 and P22, and the magnetic resonance imaging device applies more steps (of the first number) of phase encoding to the phase encoding gradients P11 and P12 corresponding to the echo Echo_1, while the magnetic resonance imaging device applies fewer steps (of the second number) of phase encoding to the phase encoding gradients P21 and P22 corresponding to the echo Echo_2, then the collected data of the echo Echo_1 can be used to reconstruct the anatomical image and the collected data of the echo Echo_2 to reconstruct the temperature image.

The first number can be arbitrarily greater than, equal to, or less than the second number, preferably greater than or equal to the second number, and most preferably greater than the second number, and the magnetic resonance imaging device can further employ the first number as a multiple of an integral number of the second number. Then, since there are more steps of phase encoding in the echo Echo_1 than in the echo Echo_2, the echo Echo_1 has a slow imaging speed and high spatial resolution, while the echo Echo_2 has a fast imaging speed and low spatial resolution.

Figure 2:
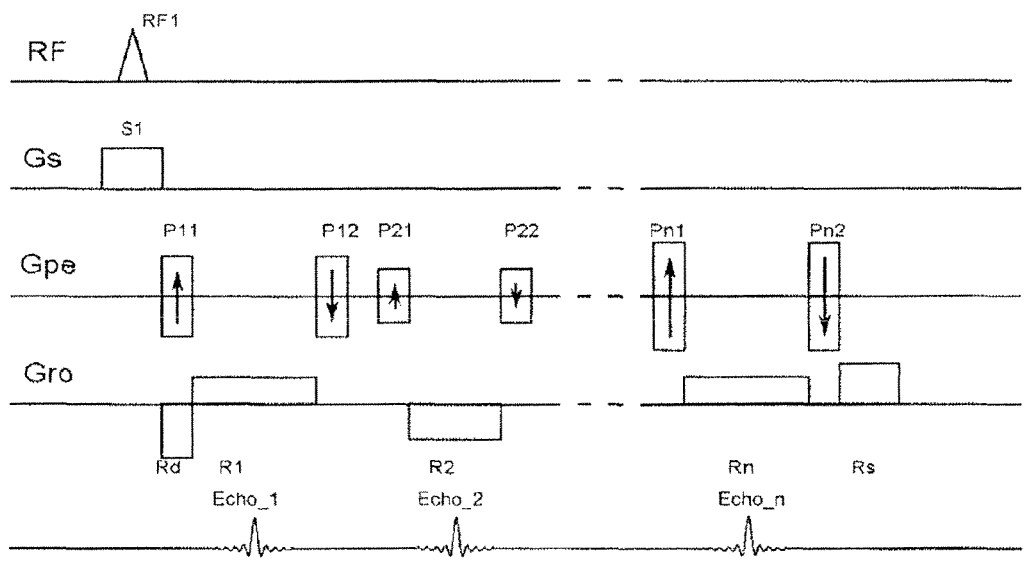
FIG. 2 is a schematic illustration of another embodiment of the present invention, in which the multi-echo sequence is formed by gradient echoes and the readout gradient employs a bi-polar mode.

As shown in FIG. 2, in another embodiment of the present invention, the multi-echo sequence also employs gradient echoes, but the readout gradients employ a bi-polar mode. Also, in FIG. 2, RF, Gs, Gpe, and Gro respectively represent a radio frequency pulse, a slice selection gradient, phase encoding gradients and readout gradients.

Similar to the embodiment shown in FIG. 1, in the embodiment shown in FIG. 2, the magnetic resonance imaging device first transmits a radio frequency pulse RF1, and at the same time applies a slice selection gradient S1.

As to the first echo Echo_1, the magnetic resonance imaging device applies a phase encoding gradient P11 in the direction of the phase encoding gradient, and applies a dephasing gradient Rd in the direction of the readout gradient. It then applies a readout gradient R1 in the direction of the readout gradient, and collects the data of the first echo Echo_1. The readout gradient R1 can be regarded as including a rephasing gradient and a dephasing gradient that are closely adjacent (not shown in detail in the figure). Finally, it applies a phase encoding gradient P12 in the direction of the phase encoding gradient.

As to the second echo Echo_2, the magnetic resonance imaging device applies a phase encoding gradient P21 in the direction of the phase encoding gradient, then applies a readout gradient R2 in the direction of the readout gradient, and collects the data of the second echo Echo_2. In the same way the readout gradient R22 can be regarded as including a rephasing gradient and a dephasing gradient that are closely adjacent (not shown in detail in the figure). Finally, it applies a phase encoding gradient P22 in the direction of the phase encoding gradient.

In the same way as in the previous embodiment, the magnetic resonance imaging device subsequently performs the operations similar to the process of the first echo and the second echo, until the magnetic resonance imaging device has collected the data of the $n^{th}$ echo Echo_n, and it applies a destruction gradient Rs in the direction of the readout gradient. By then, the magnetic resonance imaging device has applied one step of phase encoding to each echo, the readout gradients, and collected the data of each echo at the first step of phase encoding.

During the image reconstruction process, the magnetic resonance imaging device repeats the operations shown in FIG. 2, that is, it applies a first number of steps of phase encoding to the first echo, a second number of steps of phase encoding to the second echo, ..., an $n^{th}$ number of steps of phase encoding to the $n^{th}$ echo, and corresponding readout gradients, and collects the data of each echo so as to respectively reconstruct the image corresponding to each echo.

In the embodiment shown in FIG. 2, in the direction of the phase encoding gradient, the magnetic resonance imaging device can merge two adjacent phase encoding gradients as one gradient, and apply it to the target area. For example, P12 and P21, P22 and P31, ..., P(n−1)2 and Pn1 (i.e. the adjacent phase encoding gradients of adjacent echoes) are merged. In the direction of the readout gradient, the polarities of the adjacent readout gradients are opposite, therefore the magnetic resonance imaging device cannot merge them as one gradient.

Likewise, since each echo has independent phase encoding gradients and frequency encoding gradients, then the phase encoding gradients and the readout gradients corresponding to any two echoes in the multi-echo sequence can either be the same or different. For example, as shown in FIG. 2, P11 and P12 are different from P21 and P22. The magnetic resonance imaging device applies more phase encoding steps (e.g., of the first number) to the phase encoding gradients P11 and P12 corresponding to the echo Echo_1, while the magnetic resonance imaging device applies fewer phase encoding steps (of the second number) to the phase encoding gradients P21 and P22 corresponding to the echo Echo_2, then the collected data of the echo Echo_1 can be used to reconstruct the anatomical image and the collected data of the echo Echo_2 to reconstruct the temperature image. The first number is preferably greater than the second number, then since there are more phase encoding steps in the echo Echo_1 than in the echo Echo_2, the echo Echo_1 has a slow imaging speed and high spatial resolution, while the echo Echo_2 has a fast imaging speed and low spatial resolution.

Although the multi-echo sequence employs gradient echoes in the above mentioned embodiment, in practical applications, it can also employ other types of echoes, such as spin echoes. The inventors of the present invention have discovered that the imaging speed employing the gradient echoes is faster than that employing the spin echoes.

In the multi-echo sequence as shown in FIGS. 1 and 2, the data of the first echo is preferably used to reconstruct the anatomical image and the data of the second echo is used to reconstruct the temperature image in that the first echo has a relatively short echo time (TE) which can reduce the magnetic susceptibility artifacts, while the second echo has a relatively long echo time (TE) which can increase the sensitivity to the temperature change. Of course, in other embodiments, the data of the first echo can also be used to reconstruct the temperature image and the data of the second echo can be used to reconstruct the anatomical image; however, the above mentioned embodiments shown in FIG. 1 and FIG. 2 has a better sensitivity to the temperature change.

Figure 3:
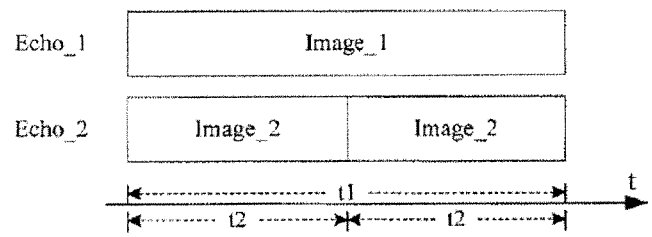
FIG. 3 is a schematic illustration of yet another embodiment of the present invention, in which the multi-echo sequence includes two echoes.

As shown in FIG. 3, this embodiment employs two echoes, with the first echo Echo_1 being used to reconstruct the anatomical image Image_1 and the second echo Echo_2 being used to reconstruct the temperature image Image_2. The number of phase encoding of the first echo Echo_1 is twice that of the second echo Echo_2, then it can be seen from the time line t that the imaging time t1 of the anatomical image Image_1 is twice the imaging time t2 of the temperature image Image_2. In other words, the imaging time t2 of the temperature image Image_2 is very short, and as a result more temperature images can be obtained during the same time period, thus improving the time resolution of the temperature image.

In the other embodiments of the present invention, the multi-echo sequence can include more than two echoes, in which, preferably, the data of the first echo are used to reconstruct the anatomical image, and the data of any echo or a plurality of echoes after the first echo are used to reconstruct the temperature image.

Figure 4A:
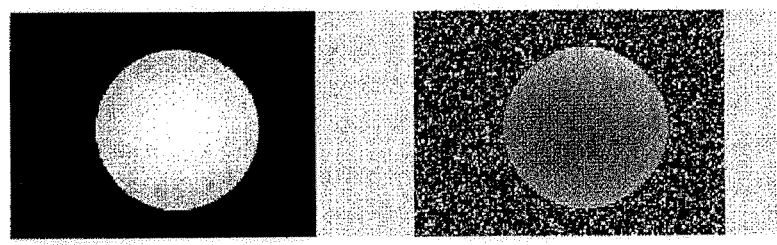
Figure 4B:
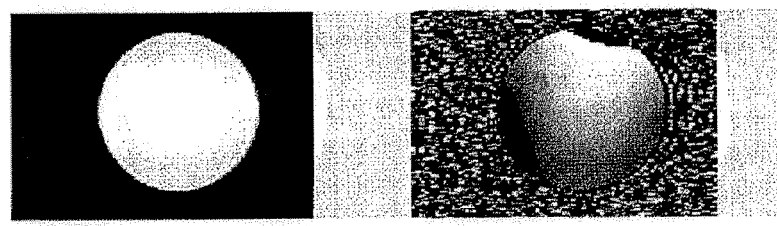
Figure 4C:
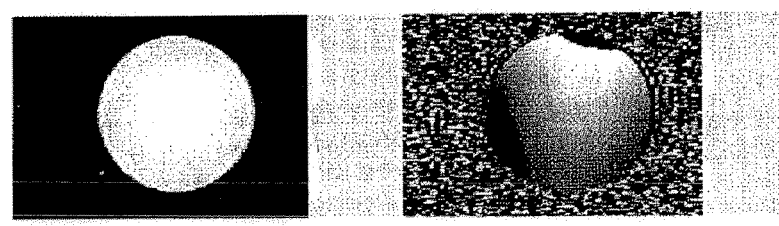
Figure 4D:
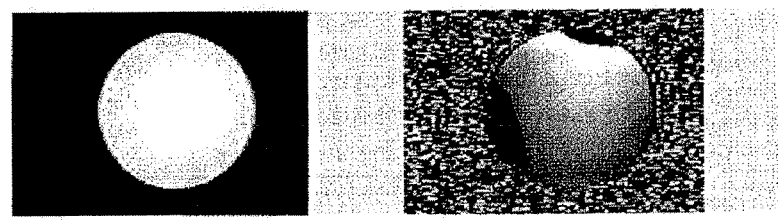

The embodiments shown in FIGS. 4a to 4b employ two echoes. FIG. 4a is the anatomical image obtained by collecting the signals of the first echo Echo_1, and FIGS. 4b, 4c and 4d are three successive temperature images obtained by collecting the signals of the second echo Echo_2 at the same time when collecting the anatomical images. In these embodiments 192 phase encoding steps are applied to the echo Echo_1 and 64 phase encoding steps are applied to the echo Echo_2, therefore the imaging time of the echo Echo_1 is three times that of the echo Echo_2, and as a result, one anatomical image and three temperature images can be respectively obtained during the same time period, with the imaging of the temperature image having relatively high time resolution. On the other hand, although the imaging of the anatomical image is relatively slow, it has relatively high spatial resolution. Therefore, the present invention achieves at the same time the acquisition of an anatomical image with high spatial resolution and a temperature image with high time resolution.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for magnetic resonance imaging, in which a magnetic resonance imaging device employs a multi-echo imaging sequence, the method further comprising:
    applying, to one echo of the multiple echoes, a first number of steps of phase encoding, applying a readout gradient, and collecting the data of this one echo to reconstruct an anatomical image; and
    applying, to another echo of the multiple echoes, a second number of steps of phase encoding, applying a readout gradient, and collecting the data of this other echo to construct a temperature image.

2. The method according to claim 1, comprising emitting said readout gradient in a mono-polar mode.

3. The method according to claim 2, comprising operating the magnetic resonance imaging device to merge a rephasing gradient and a dephasing gradient adjacent to the readout gradient direction as one gradient and to apply said one gradient.

4. The method according to claim 1, comprising emitting said readout gradient in a bi-polar mode.

5. The method according to claim 4, comprising operating the magnetic resonance imaging device to merge two gradients adjacent to the phase encoding gradient direction as one gradient and to apply said one gradient.

6. The method according to claim 1, comprising employing a phase encoding gradient applied to said one echo that is different from the phase encoding gradient applied to said other echo.

7. The method according to claim 1, comprising employing a readout gradient applied to said one echo that is different from the readout gradient applied to said other echo.

8. The method according to claim 1, comprising using, as said one echo, a first echo of said multi-echo sequence, and using, as said other echo, any one of said multi-echo sequence after said first echo.

9. The method according to claim 1, comprising using, as said other echo, a second echo of said multi-echo sequence.

10. The method according to claim 1, comprising forming said multi-echo sequence from gradient echoes or spin echoes.

11. The method according to claim 1, wherein said first number is larger than said second number.

12. The method according to claim 1 wherein said first number is a multiple of an integer number of said second number.

* * * * *